(12) United States Patent
Bischof

(10) Patent No.: US 12,415,046 B2
(45) Date of Patent: Sep. 16, 2025

(54) INSUFFLATION DEVICE AND OPERATING METHOD THAT CAN BE CARRIED OUT THEREWITH

(71) Applicant: W.O.M. WORLD OF MEDICINE GMBH, Berlin (DE)

(72) Inventor: Jan Bischof, Berlin (DE)

(73) Assignee: W.O.M. WORLD OF MEDICINE GMBH, Berlin (DE)

( * ) Notice: Subject to any disclaimer, the term of this patent is extended or adjusted under 35 U.S.C. 154(b) by 1217 days.

(21) Appl. No.: 17/058,752

(22) PCT Filed: May 27, 2019

(86) PCT No.: PCT/DE2019/000149
§ 371 (c)(1),
(2) Date: Nov. 25, 2020

(87) PCT Pub. No.: WO2019/223826
PCT Pub. Date: Nov. 28, 2019

(65) Prior Publication Data
US 2021/0213214 A1    Jul. 15, 2021

(30) Foreign Application Priority Data
May 25, 2018    (DE) .................... 10 2018 004 211.2

(51) Int. Cl.
*A61M 13/00* (2006.01)
*A61M 39/24* (2006.01)

(52) U.S. Cl.
CPC .......... *A61M 13/003* (2013.01); *A61M 39/24* (2013.01); *A61M 2039/2413* (2013.01); *A61M 2202/02* (2013.01); *A61M 2205/07* (2013.01); *A61M 2205/3344* (2013.01); *A61M 2205/50* (2013.01); *A61M 2205/75* (2013.01); *A61M 2210/1021* (2013.01)

(58) Field of Classification Search
CPC .. A61M 13/00; A61M 13/003; A61M 13/006; A61M 2039/2413; A61M 2205/07; A61M 2205/75; A61M 2205/3334
See application file for complete search history.

(56) References Cited

U.S. PATENT DOCUMENTS 6,299,592 B1 * 10/2001 Zander ................ A61M 13/003
600/560
2016/0106934 A1    4/2016 Kunitoshi
2016/0317764 A1 * 11/2016 Köth ................... A61M 13/003

FOREIGN PATENT DOCUMENTS

| DE | 4240758 A1 | 6/1993 |
| DE | 4339876 A1 | 5/1995 |
| DE | 19510712 A1 | 9/1996 |
| WO | 2011041387 A1 | 4/2011 |
| WO | 2015043570 A1 | 4/2015 |

* cited by examiner

*Primary Examiner* — Michael J Tsai
*Assistant Examiner* — Justin L Zamory
(74) *Attorney, Agent, or Firm* — Stuart H. Mayer; Kaplan Breyer Schwarz LLP

(57) ABSTRACT

The present invention relates to an insufflator with integrated flue gas extraction. Thanks to a novel valve regulation system, it is possible to direct the gas inflow through two tubes into the body cavity. The novel device also enables an improved pressure control of the body cavity, which leads to lower pressure variations in the body cavity and furthermore compensates higher leakage volume flows.

8 Claims, 2 Drawing Sheets

INSUFFLATION DEVICE AND OPERATING METHOD THAT CAN BE CARRIED OUT THEREWITH

The present invention relates to an insufflator with integrated flue gas extraction. Thanks to a novel valve regulation system, it is possible to direct the gas inflow through two tubes into the body cavity. The novel device also enables an improved pressure control of the body cavity.

BACKGROUND AND PRIOR ART

Insufflators with the possibility of simultaneous flue gas extraction are known in the art (see, e.g., WO 2015/043570 A1). This insufflator includes a tube, through which a medical gas is introduced into a body cavity (e.g., an abdomen). The gas produces a positive pressure, which expands the body cavity, in order that there is sufficient space for the visual inspection or the therapeutic intervention. Through a second tube, the gas is extracted again from the abdomen. In the case of therapeutic interventions by means of electri-cal surgery or laser, harmful flue gases may be gener-ated that are discharged and filtered by the insufflator through this second tube.

In the practice, it was found out that in certain situations, the insufflators known in prior art have drawbacks. As an example, larger leakages may occur during the surgery. Here, gas volume flows are re-quired that are far above the maximum power of known devices of 20 to 30 liters/minute. This limitation cannot, for safety reasons, simply be overcome by adjustment of a higher input pressure. The increase of the input pressure would lead to an increase of the risk for the patient.

Therefore, the present invention relates to an insufflator for the minimally invasive surgery, comprising
 a) a gas connection for a gas bottle or domestic gas (1),
 b) a first pressure and flow control unit equipped with a proportional valve and a pressure sensor (3),
 b) an in-feed line (4, 6) with filter (5) and connection to a first trocar (7),
 c) a second trocar (8) with the tube (9) and the filter (10), connected to an extraction device with variable extraction power (14),
 d) an electronic control unit,
characterized by another line (19, 17) in the insufflator, which branches off between the gas supply (1) and the first pressure and flow control unit (3) and leads via a second pressure and flow control unit (18) to the extraction line between the filter (10) and the extraction device (14), so that via the tube (9) and the trocar (8), an additional gas supply to the patient is enabled, wherein optionally between the filter (10) and the extraction device (14), a shut-off valve (13) is provided.

In contrast to prior art insufflators, the insufflator according to the invention comprises, therefore, two pressure and flow control units each with a proportional valve and a pressure sensor.

Normally, the insufflator is operated as described in the prior art (WO 2015/043570 A1). The gas connection extends via the first pressure and flow control unit to the first in-feed line. In the pressure and flow unit, a pressure sensor is provided, in order to moni-tor the pressure in the line. Further, a filter for protection of the patient is provided. The first in-feed line terminates in a first trocar that can fill the body cavity with gas. The insufflator further comprises a second tube that normally serves as an extraction tube. A second trocar introduced into the body cavity is connected by means of this extraction tube to the insufflator. The extraction tube, too, comprises a filter and leads to an extraction pump. The extraction power of the extraction pump is elec-tronically variable. The control unit is configured to keep the pressure in the body cavity as constant as possible.

In an optional embodiment of the invention, there is no extraction pump in the insufflator housing. Rather, an external pump is used, e.g., a wall extraction sys-tem as is usual in hospitals. In this case, the insufflator housing comprises a control valve, which controls the gas flow of the extraction. Of course, it is possible that the insufflator comprises both op-tions (extraction pump and connection to an external pump).

The maximum volume flow of such a device is, due to various limitations, typically between 20 and 30 lpm (liters/minute). A higher volume flow would require a higher pressure and/or trocars with larger diameters. Both are not desirable, due to safety and handling reasons. In the practice, however, situations occur, in which the maximum volume flow is not sufficient to maintain the desired target pressure in the body cavity. In this case, up to now, the surgery had to be paused and the leakage had to be closed, or the surgery was continued at a lower pressure in the cavity. The insufflator according to the invention includes, for such situations, a second pressure and flow control unit with proportional valve. By means of a control valve, it is possible to separate the extraction pump from the extraction tube and instead use the extraction tube as a second supply tube. As a result, thus, gas can also be supplied via the second tube, so that a doubled maximum total volume flow of up to 40-60 liters/minute can be obtained.

Improved Pressure Measurement Method

The insufflator according to the invention also enables an improved pressure control and measurement during the insufflation. In the conventional insufflators, the pressure measurement for measuring the pressure in the body cavity is performed by a sensor that is located at the insufflator-side end of the tube in the pressure and flow control unit. In order to be able to measure the pressure in the body cavity, the insufflation is interrupted for several hundred milliseconds. During this time, a pressure equalization between the body cavity and the tube content is obtained, which then can be measured. Thereby, the pressure in the body cavity can be determined sufficiently precisely, without having to use a pressure sensor in the body cavity. After completion of the pressure measurement, the insufflation is continued. In this way, a pulsatile gas supply occurs, with measurement phases alternating with insufflation phases. This change is not critical for body cavities of normal sizes (e.g., abdomen). For smaller body cavities, such as the rectum, this mode of operation will lead, however, to induced pressure variations in the body cavity.

The insufflator according to the invention permits an improved mode of operation: In the insufflator according to the invention, too, the gas supply in the in-feed line is interrupted for the time of the pressure measurement. Simultaneously with the interruption, the gas supply is passed through the second line. This kind of gas supply permits an undisturbed measurement of the pressure in the cavity by the first pressure sensor, with simultaneous continuation of the gas inflow.

Figure 1:
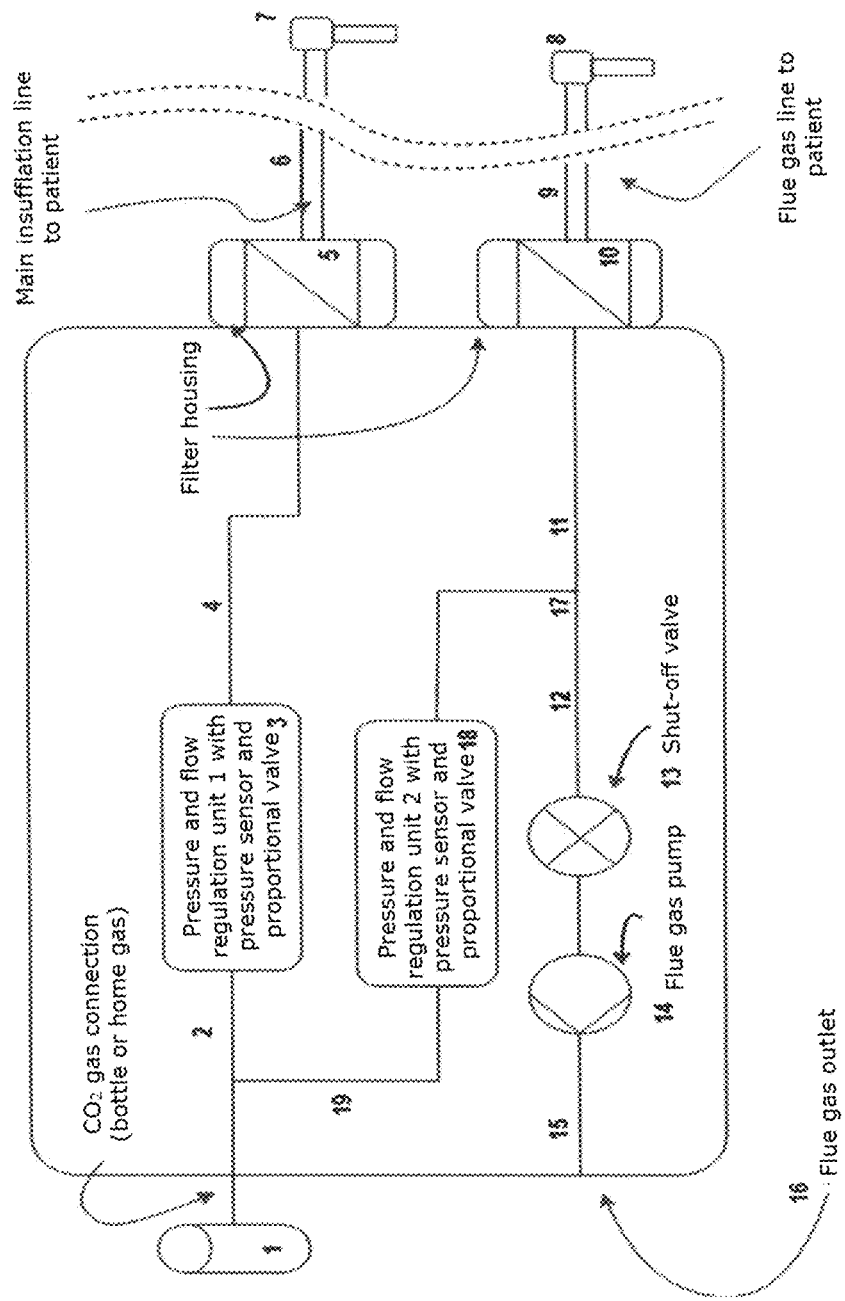
FIG. 1 shows a schematic diagram of an insufflator for use in minimally invasive surgery.

The device according to the invention is illustrated in FIG. 1. To begin with, the gas supply (1) is shown (e.g., a $CO_2$ bottle). The gas supply line (2) leads inside of the insufflator to a first pressure and flow control unit (3). In the pressure and flow unit, there are a proportional valve, a pressure sensor, and a flow sensor. The line (4) extends to a filter (5) at the outlet of the housing. By means of a tube (6), a trocar (7) is connected. This trocar (7) conducts the gas flow into the cavity of the patient. In the cavity of the patient, there is provided a second trocar (8). By this second trocar (8), as a rule, a gas extraction is performed. For this purpose, the trocar is connected by means of a tube (9) to another filter (10). The line (11) leads via an optional shut-off valve (13) to the extraction pump (14) and from there via a line (15) to an outlet (16) for the extracted flue gas. Between the filter (10) and the shut-off valve (13), a second pressure and flow control unit (18) is positioned by means of a T piece (17). The second pressure and flow unit is also connected via a line (19) to the gas connection (1).

Via this second line (9), insufflation gas can be supplied to the second trocar (8). The shut-off valve (13) must be closed, when the parallel insufflation via the second trocar (8) is to be performed. It goes without the shut-off valve, when the extraction pump has a sufficient resistance or inertia, and the pressure cannot be reduced via the pump. By this parallel insufflation via both trocars (7 and 8), a practically twice as high insufflation volume flow as with one line only can be obtained. This parallel insufflation permits maintaining a sufficient pressure in the patient in special cases, e.g., larger leakages. The electronic control unit is not shown in FIG. 1.

Figure 2:
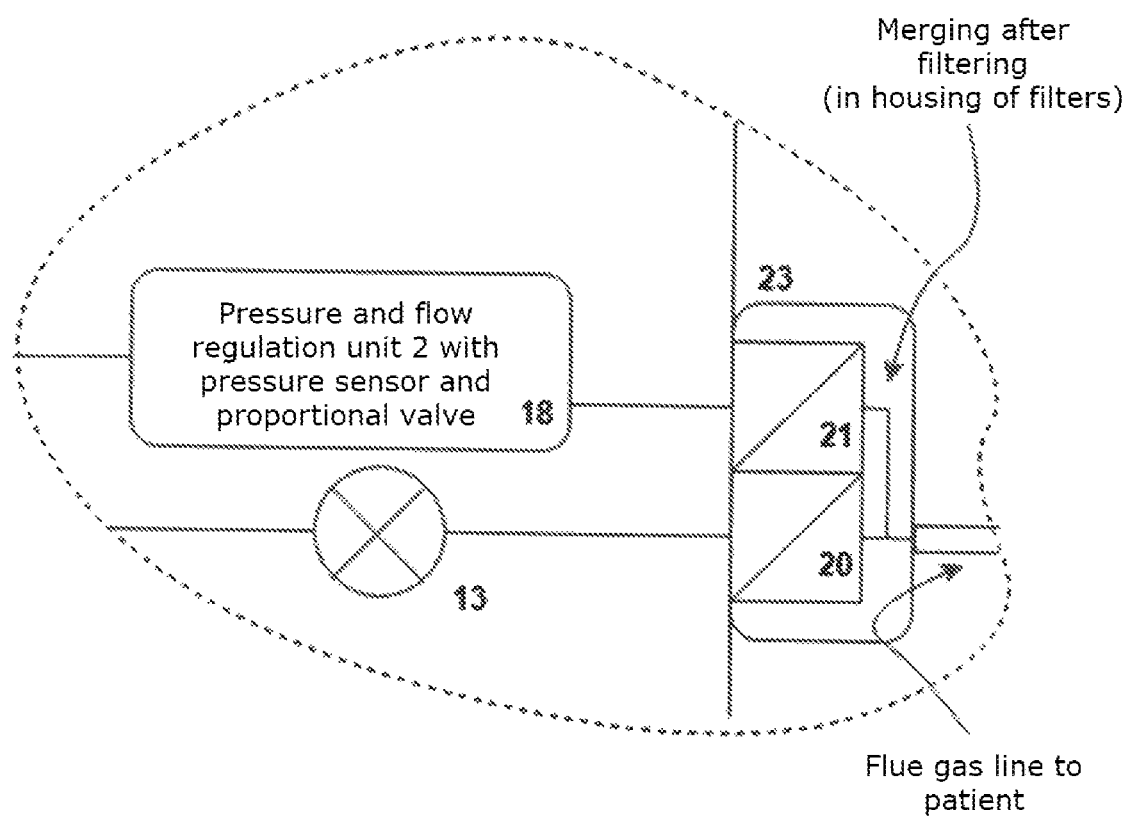
FIG. 2 shows a schematic diagram of an alternative embodiment of the insufflator.

In practical operation, the filter (10) is contami-nated with the flue gas emissions. In order to prevent that particles, and in particular germs, find their way back into the abdomen of a patient, when using the second insufflation path from the filter (10) via the trocar (8), there is of course the possibility to con-nect the line of the second pressure and flow control unit (18) behind the filter (10) only to the line to the trocar (8). For this purpose, a corresponding filter housing (23) is designed, which simultaneously enables the filtration of the flue gases via a filter (20), but also permits the connection of the gas flow of the second pressure and flow control unit (18) via a filter (21) to the trocar (8). Such a solution is shown, for example, in FIG. 2.

The insufflation unit according to the invention also permits an improved pressure measurement in regular operation. As explained above, for the purpose of the pressure measurement, the valve at the pressure sensor in the pressure and flow unit (3) is closed for several hundred milliseconds. After pressure equalization between the cavity of the patient and the line system, the pressure is detected by the pressure sensor. After pressure measurement, the proportional valve in the pressure and flow unit (3) is re-opened, and the insufflation is continued. During the pressure measurement, there is no further insufflation possible in the conventional insufflators. The insufflator according to the invention enables a continuous insufflation by the following method of operation:

For the purpose of the pressure measurement, the proportional valve in the first pressure and flow control unit (3) is closed. At the same time, the valve in the second pressure and flow control unit (18) is opened, so that the insufflation is performed for several hundred milliseconds with the same insufflation power via the trocar (8). When a flue gas extraction occurs, the shut-off valve (13) can be closed for the time of the pressure measurement. After completed pressure measurement, the proportional valve in the second pressure and flow control unit (18) is re-closed, and the proportional valve in the first pressure and flow control unit (3) is re-opened. If necessary, the control valve (13) is also re-opened, so that a flue gas extraction is possible. The advantage of this method of operation is that a continuous insufflation is obtained, and thus the pressure in the cavity varies significantly less than with conventional methods.

The invention claimed is:

1. A medical assembly for use in minimally invasive surgery, comprising:
   an insufflator which includes:
      a gas supply line 2 for receiving a gas supply;
      a first pressure and flow control unit 3 equipped with a proportional valve and a pressure sensor, the first unit adapted and configured to receive at least a portion of the gas supply from the gas supply line;
      a second pressure and flow control unit 18 equipped with a second proportional valve and a second pressure sensor, the second unit adapted and configured to receive at least a second portion of the gas supply from the gas supply line;
      an in-feed line 6 with filter 5 operatively connected to the first pressure and flow control unit 3;
      an extraction line 11 with filter 20 operatively connected to an extraction device;
      a secondary gas supply line 19 extending between the gas supply line 2 and the second pressure and flow control unit 18, and
      an electronic control unit;
   a first trocar 7 connected to a distal end of the in-feed line 6, and
   a second trocar 8 connected to a distal end of the extraction line 11,
      a secondary insufflation line with filter 21 operatively connected to the second pressure and flow control unit 18 and the second trocar 8.

2. The medical assembly as recited in claim 1, wherein the insufflator further includes a shut-off valve operatively arranged between the extraction device and the extraction line.

3. The medical assembly as recited in claim 1, wherein the extraction device is part of the insufflator.

4. The medical assembly as recited in claim 3, wherein the extraction device has variable extraction power.

5. The medical assembly as recited in claim 1, wherein the filter associated with the extraction line includes a flue gas filter and a separate supply gas filter.

6. A method for pressure measurement in a patient cavity during insufflation using the medical assembly according to claim 2, comprising the steps of:
   closing the proportional valve in the first pressure and flow control unit;
   opening the second proportional valve in the second pressure and flow control unit;
   closing the shut-off valve;
   supplying insufflating gas to the patient using the second pressure and flow control unit via the second trocar; and
   measuring a patent cavity pressure using the pressure sensor associated with the first pressure and flow control unit while the insufflating gas is being supplied to the patient via the second trocar.

7. A method for providing insufflation gas to a patient using the medical assembly according to claim 1, comprising the steps of:
  closing the shut-off valve;
  opening the second proportional valve in the second pressure and flow control unit so that a second portion of the gas supply from the gas supply line is provided to the extraction line and to the second trocar.

8. The method according to claim 7, wherein a maximum gas volume flow from the insufflator to the patient is approximately doubled when the gas is supplied via both the first and second trocars in comparison to when the gas is only supplied via the first trocar.

\* \* \* \* \*